United States Patent [19]

Yamada

[11] Patent Number: 4,558,953
[45] Date of Patent: Dec. 17, 1985

[54] COLORIMETRIC METHOD AND APPARATUS

[75] Inventor: Takashi Yamada, Hachioji, Japan
[73] Assignee: Olympus Optical Co., Ltd., Tokyo, Japan
[21] Appl. No.: 444,156
[22] Filed: Nov. 24, 1982
[30] Foreign Application Priority Data Nov. 28, 1981 [JP] Japan .................................. 56-191545

[51] Int. Cl.$^4$ ............................................... G01J 3/50
[52] U.S. Cl. .................................... 356/409; 356/414; 356/418
[58] Field of Search ............... 356/402, 409, 414, 416, 356/418, 419, 425, 243, 432; 250/226

[56] References Cited

U.S. PATENT DOCUMENTS 2,051,320  8/1936  States ................................ 250/226 X
2,421,344  5/1947  Mass ................................... 250/226 X
2,447,985  8/1948  Mass ...................................... 250/226
3,569,721  3/1971  Goldberg et al. .................... 356/306

Primary Examiner—F. L. Evans
Attorney, Agent, or Firm—Parkhurst & Oliff

[57] ABSTRACT

In a colorimeter for use in a biochemistry field, an amount of transmitted light impinging upon a light receiving device is decreased corresponding to an absorbance of a reagent to be used by arranging a light adjusting device in the optical path. The amount of light transmitted through a blank cuvette is made substantially equal to an amount of light transmitted through the reagent. Therefore, even when the analysis is performed for an item using a high absorbance reagent, the deviation of the amount of transmitted light does not affect measured absorbance values, and thus it is possible to perform the color measurement in an accurate manner regardless of the reagent absorbance.

8 Claims, 4 Drawing Figures

COLORIMETRIC METHOD AND APPARATUS

BACKGROUND OF THE INVENTION

The present invention relates to a colorimetric method for effecting a quantitative analysis for specific substances contained in a sample and an apparatus for carrying out the colormetric method.

Such a colorimetric method has been widely used in the biochemistry field, etc. In a conventional colorimetric apparatus, it is necessary to perform a 100% adjustment for a transmitted light flux (zero adjustment of an absorbance) by using water, etc. In the case of performing a photometric measurement with the aid of a reagent having extremely small absorbance, there occurs no problem due to this 100% adjustment, but in the case of using a reagent having high absorbance, measuring results might be largely affected by the absorbance of the reagent. Therefore, recently, the 100% adjustment has been generally effected by using the reagent to be used in measurement.

GOT (Glumatate Oxalacetate Transaminase) and GPT (Glumatate Pyruvate Transaminase) contained in a blood sample have been measured in an ultraviolet colorimetric (performing the photometric measurement by using ultraviolet light). In this ultraviolet colorimetric measurement, the absorbance is decreased in accordance with the reaction of GOT or GPT with the reagent, and thus when the 100% adjustment, i.e. zero absorption adjustment is performed by using the reagent, it is not possible to effect the colorimetric measurement, because the absorbance decreases below zero. Therefore, in this case, the photometric measurement is performed by deriving a difference between the transmitted light flux of the reagent and that after a sample reaction. However, since this method uses the reagent having the high absorbance, it is not possible to effect an accurate photometric measurement. This reason will be explained hereinafter.

In FIG. 1, among various test-items showing a general increasing tendency of the absorbance, a curve A shows an absorbance variation of a glucose which is selected as a type using a low absorbance reagent, and a curve B shows the absorbance variation of a magnesium which is a typical item using a high absorbance reagent. Here, both of them are measured by using a light flux having 500 nm wavelength. Table 1 shows a transmissivity and the absorbance, in the case of taking a measurement of only the reagent or after the reaction between the sample and the reagent.

TABLE 1

|  |  | reagent | after reaction |
| --- | --- | --- | --- |
| glucose | transmissivity | 89.1% | 14.1% |
|  | absorbance | 0.05 | 0.85 |
| magnesium | transmittivity | 8.96% | 6.31% |
|  | absorbance | 1.05 | 1.20 |

In Table 1, the absorbance is calculated by a formula $\log I_0/I$, where $I_0$ is the intensity of an incident light flux and I is that of a transmitted light flux. Therefore, for example, in the case of performing the photometric measurement only for the reagent used in measuring the glucose, since the incident light is 100% and the transmitted light is 89.1%, the absorbance of this reagent is obtained from the calculation $\log 100/89.1 \cong 0.05$.

After reaction between the glucose and the reagent, the transmissivity is decreased to 14.1% and the absorbance is increased to 0.85. In this case, if it is assumed that the transmissivity is varied by 0.1%, i.e. the transmissivity becomes 14.2%, the absorbance becomes $\log 100/14.2 = 0.847$ and thus an amount of the absorbance deviation becomes $0.85 - 0.847 = 0.003$. Contrary to this, in the magnesium measurement, when the transmissivity is varied by the same amount of 0.1% and is changed from 6.31% to 6.41%, the absorbance becomes $\log 100/6.41 \cong 1.193$ and thus the amount of the absorbance deviation becomes 0.007. Therefore, the amount of the absorbance deviation in the magnesium measurement is larger than that in the glucose measurement.

Moreover, in the case of performing the photometry for the reagent, if it is assumed that the transmissivity is varied by 0.1%, the amount of the absorbance deviations in the glucose measurement and the magnesium measurement become 0.0005 and 0.005, respectively. Therefore, in this case, the amount of the absorbance deviation in the magnesium measurement is larger by 10 times than that of the glucose measurement. In the case of performing the photometry by using the high absorbance reagent, slight variation and error in the amount of transmitted light affect largely the absorbance measurement as compared with the case using the low absorbance reagent, even if the 100% adjustment is performed by using the reagent. Therefore, an accuracy of the result is varied in accordance with the test-items.

Contrary to this, in the case of performing the ultraviolet colorimetric measurement for the GOT or the GPT, the absorbance after reaction between the sample including the GOT or the GPT and the reagent having the high absorbance such as 1.0–1.5 is decreased by 0.2–0.3 as compared with that for only reagent. Moreover, in an extreme case, the decreased amount of the absorbance after reaction becomes 0.7–0.8. If the absorbance is assumed to be a, an equation $I = I_0/10^a$ is derived from an equation $\log I_0/I = a$. Therefore, if the absorbance is decreased by 0.3, the amount of the transmitted light flux is increased by $1/10^{-0.3} (= 10^{0.3})$ times, i.e. about two times. In the same manner, if the absorbance is decreased by 0.5 and 0.7, respectively, the amount of transmitted light is increased by about three $(= 10^{0.5})$ and five $(= 10^{0.7})$ times, respectively. Since the larger the amount of transmitted light becomes, the better an S/N ratio becomes, the accuracy of the photometric measurement is improved. However, if the deviation of the amount of transmitted light becomes large as mentioned above, the S/N ratio, i.e. the accuracy, is varied correspondingly, and thus the accuracy of the colorimetric measurement cannot be stably maintained.

SUMMARY OF THE INVENTION

The present invention has for its object to eliminate the drawbacks mentioned above and to provide a colorimetric method which can maintain the accuracy of the colormetric measurement stable regardless of the test-items by varying the amount of the incident light flux depending upon the test item.

According to the invention, a colorimetric method for performing a quantitative analysis for specific substances contained in a sample comprises the steps of:

effecting a 100% transmissivity adjustment, i.e. a zero absorbance adjustment, for a blank with an amount of light which is predetermined depending upon an absorbance of a reagent to be used:

taking a photometric measurement of the absorbance of the reagent with the maximum amount of light; and taking a photometric measurement of an absorbance of a reacted sample solution with the maximum amount of light.

Another object of the invention is to provide a colorimetric apparatus for performing the colorimetric method mentioned above in a positive and precise manner by arranging a light adjusting means.

According to the invention, in a colorimetric apparatus comprising a light source projecting a light beam onto a photometric cuvette containing a reagent and a sample solution therein and a light receiving device for receiving the light beam transmitted through the cuvette, the improvement comprises:

means arranged in an optical path between the light source and the light receiving device for selectively adjusting an amount of the light beam impinging upon the light receiving device in such a manner that an amount of the light beam transmitted through a blank cuvette and the light adjusting means becomes substantially equal to an amount of the light beam transmitted through the cuvette containing the reagent.

DESCRIPTION OF THE PREFERRED EMBODIMENTS

Figure 2:
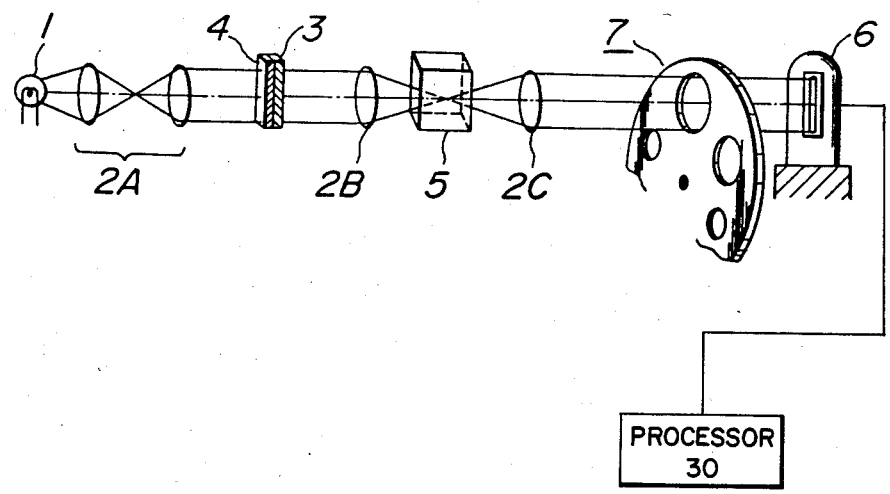
FIG. 2 is a schematic view illustrating a construction of an embodiment of the colorimetric apparatus according to the invention.

FIG. 2 is a schematic view showing one embodiment of the colorimeter apparatus according to the invention. In FIG. 2, the apparatus comprises a light source 1, a collimating lens system 2A, an optical filter 3, an N.D. filter 4 which can be selectively inserted in an optical path for adjusting the amount of light, a condenser lens 2B, a collecting lens 2C, a photometric cuvette 5 in which a sample and a reagent are contained and a light receiving device 6. Further, according to the invention, a light adjusting device 7 is arranged between the cuvette 5 and the light receiving device 6.

Figure 3:
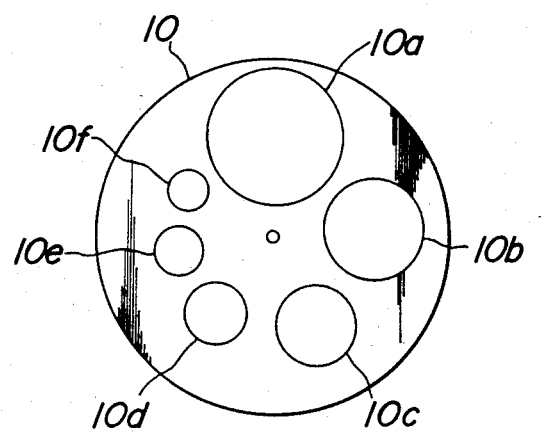
FIGS. 3 and 4 are schematic views showing first and second embodiments of a light adjusting device according to the invention.

FIG. 3 is a schematic view showing a first embodiment of the light adjusting device according to the invention. In FIG. 3, the light adjusting device comprises a disc 10 in which a plurality of apertures 10a, 10b, 10c, 10d, 10e and 10f having different radii are formed along a circle, each of these apertures constituting an iris. These apertures have different areas which are so determined that an amount of light transmitted through the apertures varies as shown in table 2. In table 2, a ratio of the amount of transmitted light and an absorbance are represented on the basis of the amount of transmitted light and the absorbance of the largest aperture 10a. That is to say, the absorbance may be selected from 0.0, 0.2, 0.4, 0.6, 0.8 and 1.0 by selectively inserting the apertures 10a, 10b, 10c, 10d, 10e and 10f.

TABLE 2

| aperture | 10a | 10b | 10c | 10d | 10e | 10f |
| --- | --- | --- | --- | --- | --- | --- |
| ratio of the amount of transmitted light | 100% | 63.1% | 39.8% | 25.1% | 15.8% | 10.0% |

TABLE 2-continued

| aperture | 10a | 10b | 10c | 10d | 10e | 10f |
| --- | --- | --- | --- | --- | --- | --- |
| absorbance | 0.0 | 0.2 | 0.4 | 0.6 | 0.8 | 1.0 |

According to the invention, during the 100% transmissivity adjustment, i.e. the zero absorbance adjustment, by using the blank cuvette, any desired one of the apertures 10a to 10f is inserted into the optical path dependent upon the absorbance of a reagent to be used. That is to say, when the reaction is an absorbance increasing one, it is preferable to select the aperture in such a manner that an amount of light transmitted through the blank cuvette and the relevant aperture is a little larger than an amount of light transmitted through the cuvette containing the reagent and the largest aperture 10a. Contrary to this, when the reaction is an absorbance decreasing one, a desired aperture is so selected that an amount of light transmitted through the blank cuvette and the relevant aperture is slightly larger than an amount of light transmitted through the cuvette containing the reagent and sample and the largest aperture 10a. In general, the desired aperture can be previously determined for respective test items, based upon the absorbances to be used, the direction of the absorbance change, i.e. increase or decrease, and an amount of the absorbance change during the reaction.

Now some examples of the colorimetric method according to the invention will be explained.

EXAMPLE 1

Figure 1:
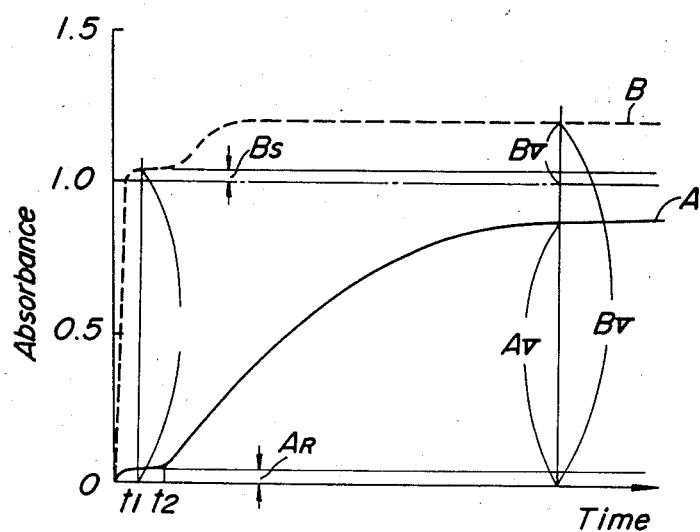
FIG. 1 is a graph showing a coloring characteristic in a colorimetry colorimetric measurement of a glucose and a magnesium.

When an analysis is to be performed for an item using a low absorbance reagent such as a glucose shown by the line A in FIG. 1, at first the largest aperture 10a having the ratio of 100% (absorbance 0.0) is inserted in the optical path, and then the colorimetric measurement (absorbance measurement) is performed normally. In this case, since the reagent absorbance is low, the measurement could hardly be affected by a slight deviation and error of the amount of transmitted light for the reagent. After setting the aperture 10a having the absorbance of 0.0, 100% adjustment of the transmitted light flux is performed with respect to the blank cuvette containing water or nothing. Then the reagent is supplied into the cuvette and the absorbance measurement for the reagent is effected at a time $t_1$ so as to obtain an absorbance value $A_R$ of the reagent. Next, at a time $t_2$ a sample solution is supplied into the cuvette, and then at a time $t_3$ when the sample solution is in a stationary condition after reacting with the reagent, the absorbance measurement for the reacted solution is performed so as to obtain the absorbance value $A_V$ for the reacted solution. Finally, the absorbance value $A_T$ for the relevant test item A is derived from a calculation ($A_V$-$A_R$). These processes mentioned above are effected electrically by means of a processor 30 which treats an electric output supplied from the light receiving device 6.

EXAMPLE 2

When an analysis is to be performed by using a high absorbance reagent for a test item such as magnesium shown by the line B in FIG. 1, at first the 100% adjustment is performed with respect to the blank cuvette, while the smaller aperture 10f is inserted in the optical path. In this case, an amount of light transmitted through the blank cuvette and the aperture 10f is slightly larger than an amount of light transmitted through the reagent for use in the magnesium analysis and the largest aperture 10a. In the case of the magnesium analysis, since the absorbance shows an increasing coloring characteristic in accordance with the reaction, the absorbance value of the aperture 10f is set a little lower than the reagent absorbance. In this manner, while aperture 10f (absorbance 1.0) is set in the optical path, the 100% adjustment is performed. Therefore, in this case, when the 100% adjustment for the blank is effected, only 10% light flux with respect to the standard amount of light transmitted through the largest aperture 10a is made incident upon the light receiving device 6.

Then, only the reagent is delivered into the cuvette, and at the time $t_1$ the reagent absorbance is measured, while the largest aperture 10a having the absorbance 0.0 is inserted in the optical path. In the conventional colorimetric method for the magnesium analysis, the reagent absorbance value $B_R$ is 1.05 and the amount of transmitted light is 8.91%. However, according to the invention, since the colorimeter apparatus is calibrated by using the 10% light flux with respect to the fully opened aperture 10a of 100%, the amount of transmitted light and the reagent absorbance value ($B_S$) is measured as 89.1% and 0.05 respectively.

Next, at the time $t_2$ the sample solution is delivered into the cuvette, and then at the time $t_3$ when the sample solution is in a stationary condition after reacting with the reagent, the absorbance for the reacted solution is measured, while the largest aperture 10a remains in the optical path. In the conventional colorimeteric method, the amount of transmitted light and the absorbance of the sample solution after reaction are measured as 6.31% and 1.20, respectively (see table 1), but according to the invention these values become 63.1% and 0.2 ($B_V$), respectively. Correspondingly, the absorbance value $B_T$ for the magnesium is derived from the calculation ($B_V - B_S$). In the case that the amount of transmitted light is measured as 63.1%, even if the amount of transmitted light is varied by 0.1%, the corresponding absorbance deviation is 0.001 and this deviation 0.001 is extremely small as compared with that of the conventional colorimetry (0.007 in the conventional colorimetry). Therefore, according to the invention, the deviation and error of the transmitted light flux do not substantially affect the photometric measurement value.

EXAMPLE 3

When the colorimetric measurement is to be performed for an item such as GOT and GPT wherein the absorbance shows a decreasing coloring characteristic in accordance with the reaction with the reagent, the 100% adjustment of the transmitted light flux for the blank cuvette is performed while taking into account the reagent absorbance and the absorbance deviation of the reacted sample solution. That is to say, a desired aperture is so selected that an amount of light transmitted through the blank cuvette and the relevant aperture is a little larger than an amount of light transmitted through the reacted solution and the largest aperture 10a. After that, the colorimetric measurement is continued in the same manner as the previous examples 1 and 2.

Figure 4:
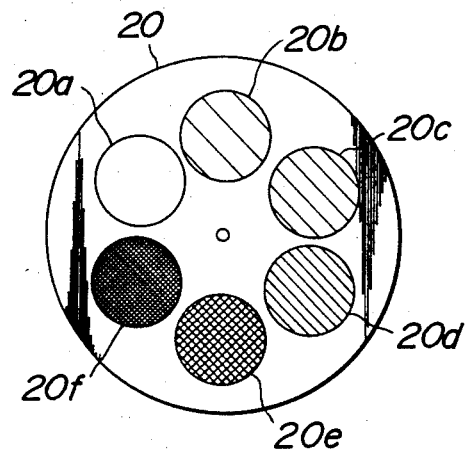

FIG. 4 is a schematic view showing another embodiment of the light adjusting device 7 according to the invention. In FIG. 4, the amount of transmitted light is controlled not by the area of the apertures, but by the optical density. The light adjusting device of this embodiment comprises a rotary disc 20 having a plurality of N.D. filters 20a to 20f arranged along a circle. Also in this case, these filters 20a to 20f have different densities so as to obtain the different absorbances shown in Table 2.

In the embodiments shown in FIGS. 3 and 4, any desired one of the apertures or filters may be selectively inserted into the optical path by rotating the disc 10 or 20 by a conventional driving means such as a motor. It should be noted that it is also possible to use an iris which has been widely used in conventional cameras. However, in order to control the amount of transmitted light precisely, the discs 10 and 20 shown in FIGS. 3 and 4 seem to be more advantageously used than the camera iris.

Moreover, the amount of transmitted light may be adjusted by controlling a lamp voltage applied to the light source, but in this case it is rather difficult to control the amount of light emitted from the light source quantitatively in an accurate manner. It should be further noted that the light adjusting device may be arranged at any point on the optical path between the light source and the light detector. According to the invention, even when the analysis is performed for the item using a high absorbance reagent, the deviation of the amount of transmitted light does not affect the measured results, and thus it is possible to perform the colorimetric measurement in an accurate and stable manner regardless of the reagent absorbance.

What is claimed is:

1. A colorimetric method for effecting a quantitative analysis for specific substances contained in a sample comprising the steps of:

placing a blank cuvette into an optical path between a light source emitting a light beam and a light receiving means for detecting said light beam;

placing a light adjusting means between said blank cuvette and said light receiving means;

selectively adjusting the amount of light transmitted through said blank cuvette to said light receiving device by adjusting said light adjusting means such that the amount of light detected by said light receiving means approximates the amount of light which will be detected by said light receiving means when absorbance of a reagent to be used is measured in said cuvette when said light adjusting means is set to allow the passage of the maximum amount of light to said light receiving means;

effecting a 100% adjustment of said transmitted light, i.e., a zero absorbance adjustment for said blank cuvette when said adjusted light is detected by said light receiving means;

supplying said reagent to said cuvette;

measuring the absorbance of said reagent while said light adjusting means allows the maximum amount of light to pass to said light receiving means;

supplying a sample to said cuvette, and reacting said sample with said reagent;

measuring the absorbance of said reacted sample while said light adjusting means allows the maximum amount of light to pass to said light receiving means; and obtaining the difference between said absorbance of said reagent and said absorbance of said reacted sample to derive the absorbance value for said sample.

2. The colorimetric method according to claim 1, wherein said adjusted light for effectuating the zero absorbance adjustment is determined to be slightly larger than the amount of light detected by said light receiving means when the absorbance of the reagent is measured.

3. The colorimetric method according to claim 2, wherein said adjusted light for effectuating the zero absorbance adjustment is determined to be slightly larger than the amount of light detected by said light receiving means when the absorbance of the reacted sample solution is measured.

4. A colorimeter comprising:
a light source emitting a light beam onto a cuvette;
a light receiving means for detecting the light beam transmitted through said cuvette, said cuvette positioned between said light source and said light receiving means; and
a light adjusting means arranged in an optical path between said light source and said light receiving device for selectively adjusting the amount of light transmitted through a blank cuvette to said light receiving device by adjusting said light adjusting means such that the amount of light transmitted through said blank cuvette and detected by said light receiving means approximates the amount of light which will be detected by said light receiving means when the absorbance of a reagent to be used is measured in said cuvette when said light adjusting means is set to allow the passage of the maximum amount of light to said light receiving means;
a means to measure the absorbance of said reagent while said light adjusting means allows the maximum amount of light to pass to said light receiving means;
a means to measure the absorbance of a reacted sample in said cuvette while said light adjusting means allows the maximum amount of light to pass to said light receiving means; and
a means to obtain the difference between said absorbance of said reagent and said absorbance of said reacted sample to derive the absorbance value for said sample.

5. The colorimeter according to claim 4, wherein said light adjusting means is arranged between said cuvette and said light receiving means.

6. The colorimeter according to claim 5, wherein said light amount adjusting means comprises a rotary disc and a plurality of apertures having different transmissivities and formed in said disc along a circle, whereby any one of the apertures can be selectively inserted into said optical path.

7. The colorimeter according to claim 5, wherein said light adjusting means comprises a rotary disc and plurality of N.D. filters having different transmissivities and arranged in said disc along a circle, whereby any one of the filters can be selectively inserted into said optical path.

8. The colorimeter according to claim 6, wherein said different transmissivities of said light adjusting means are set to 100%, 63.1%, 39.8%, 25.1%, 15.8% and 10.0%.

* * * * *